(12) United States Patent
Silvestrini et al.

(10) Patent No.: US 10,647,831 B2
(45) Date of Patent: May 12, 2020

(54) POLYMERIC MATERIAL FOR ACCOMMODATING INTRAOCULAR LENSES

(71) Applicant: LensGen, Inc., Irvine, CA (US)

(72) Inventors: Thomas Silvestrini, Alamo, CA (US); Kevin Yacoub, Irvine, CA (US)

(73) Assignee: LensGens, Inc., Irvine, CA (US)

( * ) Notice: Subject to any disclaimer, the term of this patent is extended or adjusted under 35 U.S.C. 154(b) by 0 days.

(21) Appl. No.: 15/513,502

(22) PCT Filed: Sep. 22, 2015

(86) PCT No.: PCT/US2015/051512
§ 371 (c)(1),
(2) Date: Mar. 22, 2017

(87) PCT Pub. No.: WO2016/049059
PCT Pub. Date: Mar. 31, 2016

(65) Prior Publication Data
US 2017/0247525 A1    Aug. 31, 2017

Related U.S. Application Data

(60) Provisional application No. 62/054,303, filed on Sep. 23, 2014.

(51) Int. Cl.
| | | |
|---|---|---|
| C08K 3/36 | (2006.01) | |
| C08G 77/20 | (2006.01) | |
| C08G 77/24 | (2006.01) | |
| C08L 83/08 | (2006.01) | |
| C08L 83/00 | (2006.01) | |
| A61F 2/16 | (2006.01) | |
| A61L 27/18 | (2006.01) | |
| C08J 3/24 | (2006.01) | |
| C08K 5/54 | (2006.01) | |
| C08G 77/12 | (2006.01) | |

(52) U.S. Cl.
CPC ............ C08K 3/36 (2013.01); A61F 2/16 (2013.01); A61L 27/18 (2013.01); C08G 77/20 (2013.01); C08G 77/24 (2013.01); C08J 3/24 (2013.01); C08K 5/5403 (2013.01); C08L 83/00 (2013.01); C08L 83/08 (2013.01); C08G 77/12 (2013.01); C08J 2383/08 (2013.01); C08K 2201/006 (2013.01)

(58) Field of Classification Search
CPC ....... A61F 2/16; C08G 77/24; C08L 2203/02; C08L 83/04
See application file for complete search history.

(56) References Cited

U.S. PATENT DOCUMENTS

| | | |
|---|---|---|
| 4,032,502 A | 6/1977 | Lee et al. |
| 4,373,218 A | 2/1983 | Schachar |
| 4,512,040 A | 4/1985 | McClure |
| 4,585,457 A | 4/1986 | Kalb |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,882,368 A * | 11/1989 | Elias ............... C08F 292/00 523/213 |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,059,668 A * | 10/1991 | Fukuda ............. C08G 77/24 528/15 |
| 5,074,876 A | 12/1991 | Kelman |
| 5,091,121 A | 2/1992 | Nakada et al. |
| 5,152,788 A | 10/1992 | Isaacson et al. |
| 5,167,883 A | 12/1992 | Takemasa et al. |
| 5,171,773 A | 12/1992 | Chaffee et al. |

(Continued)

FOREIGN PATENT DOCUMENTS

| | | |
|---|---|---|
| EP | 0356050 A1 | 2/1990 |
| EP | 0766540 B1 | 8/1999 |

(Continued)

OTHER PUBLICATIONS

International Preliminary Report on Patentability for International Application No. PCT/US2015/051512 dated Mar. 28, 2017. (7 pages).
Extended European Search Report for European Application No. 15844326.7 dated Apr. 26, 2018. (10 pages).
International Search Report and Written Opinion for PCT/US2015/051512 dated Jan. 13, 2016, 12 pages.
Pubchem, Substance Record for SID 184590955, Deposit Date: Jun. 23, 2014 (retrieved Dec. 28, 2015). Retrieved from the Internet: <URL: https://pubchem.ncbi.nlm.nih.gov/substance/184590955#section=Top>.
Ehrmann, et al., "Biomechanical analysis of the accommodative apparatus in primates", Clinical and Experimental Optometry, May 2008, vol. 91, Issue 3, pp. 302-312.

(Continued)

*Primary Examiner* — Nicole M. Buie-Hatcher
(74) *Attorney, Agent, or Firm* — Knobbe Martens Olson & Bear LLP

(57) ABSTRACT

The disclosure relates generally to a polymeric material for use in accommodating intraocular lenses for implantation in a lens chamber of a subject's eye. The present disclosure is directed to a polymeric material which comprises a fluorosilicone polymer and a silica component. The presently disclosed polymeric material is both optically clear and has a sufficiently low Young's modulus such that it can effectively respond to the eye's natural accommodative forces and thus can be used in accommodating intraocular lenses. When used in the fabrication of an intraocular lenses, the polymeric material disclosed herein protect the physical characteristics of the lens as the added hydrophobicity of the fluorosilicone polymer allows it to effectively resist diffusion of fluid from the eye and the adhesion of biologica materials.

21 Claims, No Drawings

(56) References Cited

U.S. PATENT DOCUMENTS

| | | |
|---|---|---|
| 5,227,447 A | 7/1993 | Sato et al. |
| 5,236,970 A | 8/1993 | Christ et al. |
| 5,264,522 A * | 11/1993 | Mize .................. C08K 3/36 |
| | | 524/493 |
| 5,275,623 A | 1/1994 | Sarfarazi |
| 5,278,258 A * | 1/1994 | Gerace .................. C08L 83/04 |
| | | 525/478 |
| 5,312,860 A | 5/1994 | Mize et al. |
| 5,336,487 A | 8/1994 | Refojo et al. |
| 5,443,506 A | 8/1995 | Garabet |
| 5,447,987 A * | 9/1995 | Sato .................. C08L 83/04 |
| | | 524/263 |
| 5,489,302 A | 2/1996 | Skottun |
| 5,583,178 A | 12/1996 | Oxman et al. |
| 5,607,472 A | 3/1997 | Thompson |
| 5,665,794 A * | 9/1997 | Maxson .................. C08L 83/08 |
| | | 523/209 |
| 5,854,310 A | 12/1998 | Maxson |
| 6,071,439 A | 6/2000 | Bawa et al. |
| 6,117,171 A | 9/2000 | Skottun |
| 6,197,057 B1 | 3/2001 | Peyman et al. |
| 6,361,561 B1 | 3/2002 | Huo et al. |
| 6,551,354 B1 | 4/2003 | Ghazizadeh et al. |
| 6,616,691 B1 | 9/2003 | Tran |
| 6,695,881 B2 | 2/2004 | Peng et al. |
| 6,730,123 B1 | 5/2004 | Klopotek |
| 6,836,374 B2 | 12/2004 | Esch et al. |
| 6,855,164 B2 | 2/2005 | Glazier |
| 6,858,040 B2 | 2/2005 | Nguyen et al. |
| 6,860,601 B2 | 3/2005 | Shadduck |
| 6,926,736 B2 | 8/2005 | Peng et al. |
| 6,930,838 B2 | 8/2005 | Schachar |
| 6,935,743 B2 | 8/2005 | Shadduck |
| 6,966,649 B2 | 11/2005 | Shadduck |
| 6,969,403 B2 | 11/2005 | Peng et al. |
| 7,041,134 B2 | 5/2006 | Nguyen et al. |
| 7,063,723 B2 | 6/2006 | Ran |
| 7,068,439 B2 | 6/2006 | Esch et al. |
| 7,122,053 B2 | 10/2006 | Esch |
| 7,150,760 B2 | 12/2006 | Zhang |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,316,713 B2 | 1/2008 | Zhang |
| 7,416,562 B2 | 8/2008 | Gross |
| 7,438,723 B2 | 10/2008 | Esch |
| 7,452,377 B2 * | 11/2008 | Watling .................. A61L 27/18 |
| | | 528/32 |
| 7,453,646 B2 | 11/2008 | Lo |
| 7,485,144 B2 | 2/2009 | Esch |
| 7,591,849 B2 | 9/2009 | Richardson |
| 7,637,947 B2 | 12/2009 | Smith et al. |
| 7,662,179 B2 | 2/2010 | Sarfarazi |
| 7,675,686 B2 | 3/2010 | Lo et al. |
| 7,753,953 B1 | 7/2010 | Yee |
| 7,776,088 B2 | 8/2010 | Shadduck |
| 7,780,729 B2 | 8/2010 | Nguyen et al. |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,986,465 B1 | 7/2011 | Lo et al. |
| 7,998,198 B2 | 8/2011 | Angelopoulos et al. |
| 7,998,199 B2 | 8/2011 | Nun |
| 8,012,204 B2 | 9/2011 | Weinschenk, III et al. |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,062,361 B2 | 11/2011 | Nguyen et al. |
| 8,070,806 B2 | 12/2011 | Khoury |
| 8,158,712 B2 | 4/2012 | Your |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,216,306 B2 | 7/2012 | Coroneo |
| 8,246,679 B2 | 8/2012 | Nguyen et al. |
| 8,254,034 B1 | 8/2012 | Shields et al. |
| 8,257,827 B1 | 9/2012 | Shi et al. |
| 8,273,123 B2 | 9/2012 | Nun |
| 8,303,656 B2 | 11/2012 | Shadduck |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,377,124 B2 | 2/2013 | Hong et al. |
| 8,398,709 B2 | 3/2013 | Nun |
| 8,414,646 B2 | 4/2013 | De Juan, Jr. et al. |
| 8,425,597 B2 | 4/2013 | Glick et al. |
| 8,425,599 B2 | 4/2013 | Shadduck |
| 8,430,928 B2 | 4/2013 | Liao |
| 8,447,086 B2 | 5/2013 | Hildebrand et al. |
| 8,454,688 B2 | 6/2013 | Esch et al. |
| 8,475,529 B2 | 7/2013 | Clarke |
| 8,496,701 B2 | 7/2013 | Hermans et al. |
| 8,500,806 B1 | 8/2013 | Phillips |
| 8,545,556 B2 | 10/2013 | Woods et al. |
| 8,579,972 B2 | 11/2013 | Rombach |
| 8,585,758 B2 | 11/2013 | Woods |
| 8,608,799 B2 | 12/2013 | Blake |
| 8,608,800 B2 | 12/2013 | Portney |
| 8,613,766 B2 | 12/2013 | Richardson et al. |
| 8,647,384 B2 | 2/2014 | Lu |
| 8,657,878 B2 | 2/2014 | Mentak et al. |
| 8,668,734 B2 | 3/2014 | Hildebrand et al. |
| 8,690,942 B2 | 3/2014 | Hildebrand et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,858,626 B2 | 10/2014 | Noy |
| 8,867,141 B2 | 10/2014 | Pugh et al. |
| 8,900,298 B2 | 12/2014 | Anvar et al. |
| 8,900,300 B1 | 12/2014 | Wortz |
| 8,956,408 B2 | 2/2015 | Smiley et al. |
| 8,968,396 B2 | 3/2015 | Matthews et al. |
| 8,968,399 B2 | 3/2015 | Ghabra |
| 8,992,609 B2 | 3/2015 | Shadduck |
| 9,005,282 B2 | 4/2015 | Chang et al. |
| 9,005,283 B2 | 4/2015 | Nguyen et al. |
| 9,034,035 B2 | 5/2015 | Betser et al. |
| 9,044,317 B2 | 6/2015 | Hildebrand et al. |
| 9,072,600 B2 | 7/2015 | Tran |
| 9,090,033 B2 | 7/2015 | Carson et al. |
| 9,095,424 B2 | 8/2015 | Kahook et al. |
| 9,125,736 B2 | 9/2015 | Kahook et al. |
| 9,186,244 B2 | 11/2015 | Silvestrini et al. |
| 9,198,752 B2 | 12/2015 | Woods |
| 9,277,987 B2 | 3/2016 | Smiley et al. |
| 9,289,287 B2 | 3/2016 | Kahook et al. |
| 9,326,846 B2 | 5/2016 | Devita Gerardi et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,421,088 B1 | 8/2016 | Kahook et al. |
| 9,427,312 B2 | 8/2016 | DeBoer et al. |
| 9,433,497 B2 | 9/2016 | DeBoer et al. |
| 9,456,895 B2 | 10/2016 | Shadduck |

(56) References Cited

U.S. PATENT DOCUMENTS

| | | |
|---|---|---|
| 9,486,311 B2 | 11/2016 | Argento et al. |
| 9,610,155 B2 | 4/2017 | Matthews |
| 9,622,852 B2 | 4/2017 | Simonov et al. |
| 9,629,712 B2 | 4/2017 | Stenger |
| 9,636,213 B2 | 5/2017 | Brady |
| 9,655,716 B2 | 5/2017 | Cumming |
| 9,681,946 B2 | 6/2017 | Kahook et al. |
| 9,693,858 B2 | 7/2017 | Hildebrand et al. |
| 9,713,526 B2 | 7/2017 | Rombach |
| 9,713,527 B2 | 7/2017 | Nishi et al. |
| 9,717,589 B2 | 8/2017 | Simonov et al. |
| 9,744,027 B2 | 8/2017 | Jansen |
| 9,744,028 B2 | 8/2017 | Simonov et al. |
| 9,795,473 B2 | 10/2017 | Smiley et al. |
| 9,808,339 B2 | 11/2017 | Dorronsoro Diaz et al. |
| 9,814,568 B2 | 11/2017 | Ben Nun |
| 9,814,570 B2 | 11/2017 | Robert et al. |
| 9,820,849 B2 | 11/2017 | Jansen |
| 9,848,980 B2 | 12/2017 | McCafferty |
| 9,855,137 B2 | 1/2018 | Smiley et al. |
| 9,855,139 B2 | 1/2018 | Matthews et al. |
| 9,861,469 B2 | 1/2018 | Simonov et al. |
| 9,872,762 B2 | 1/2018 | Scholl et al. |
| 9,872,763 B2 | 1/2018 | Smiley et al. |
| 9,877,825 B2 | 1/2018 | Kahook et al. |
| 9,883,940 B2 | 2/2018 | Nishi et al. |
| 9,925,039 B2 | 3/2018 | Sohn et al. |
| 9,925,040 B2 | 3/2018 | Kahook et al. |
| 9,931,202 B2 | 4/2018 | Borja et al. |
| 9,987,126 B2 | 6/2018 | Borja et al. |
| 10,004,596 B2 | 6/2018 | Brady et al. |
| 10,028,824 B2 | 7/2018 | Kahook et al. |
| 10,045,844 B2 | 8/2018 | Smiley et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 10,195,018 B2 | 2/2019 | Salahieh et al. |
| 10,195,020 B2 | 2/2019 | Matthews |
| 2002/0005344 A1 | 1/2002 | Heidlas et al. |
| 2002/0055776 A1 | 5/2002 | Juan, Jr. et al. |
| 2002/0071856 A1 | 6/2002 | Dillingham et al. |
| 2002/0120329 A1 | 8/2002 | Lang et al. |
| 2003/0093149 A1 | 5/2003 | Glazier |
| 2003/0105522 A1 | 6/2003 | Glazier |
| 2003/0109926 A1 | 6/2003 | Portney |
| 2003/0158295 A1* | 8/2003 | Fukuda .................. C08F 259/08 523/216 |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0162612 A1 | 8/2004 | Portney et al. |
| 2004/0169816 A1 | 9/2004 | Esch |
| 2004/0249455 A1 | 12/2004 | Tran |
| 2005/0021139 A1 | 1/2005 | Shadduck |
| 2005/0071002 A1 | 3/2005 | Glazier |
| 2005/0107873 A1 | 5/2005 | Zhou |
| 2005/0137703 A1 | 6/2005 | Chen |
| 2005/0251253 A1 | 11/2005 | Gross |
| 2005/0251254 A1 | 11/2005 | Brady et al. |
| 2005/0267575 A1 | 12/2005 | Nguyen et al. |
| 2006/0041307 A1 | 2/2006 | Esch et al. |
| 2006/0047339 A1 | 3/2006 | Brown |
| 2006/0069178 A1 | 3/2006 | Rastogi et al. |
| 2006/0074487 A1 | 4/2006 | Gilg |
| 2006/0111776 A1 | 5/2006 | Glick et al. |
| 2006/0134173 A1 | 6/2006 | Liu et al. |
| 2006/0135477 A1 | 6/2006 | Haitjema et al. |
| 2006/0212116 A1 | 9/2006 | Woods |
| 2006/0238702 A1 | 10/2006 | Glick et al. |
| 2006/0241752 A1 | 10/2006 | Israel |
| 2007/0016293 A1 | 1/2007 | Tran |
| 2007/0032868 A1 | 2/2007 | Woods et al. |
| 2007/0050024 A1 | 3/2007 | Zhang |
| 2007/0050025 A1 | 3/2007 | Nguyen et al. |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0132949 A1 | 6/2007 | Phelan |
| 2007/0213817 A1 | 9/2007 | Esch et al. |
| 2007/0260308 A1 | 11/2007 | Tran |
| 2007/0260310 A1 | 11/2007 | Richardson |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0046077 A1 | 2/2008 | Cumming |
| 2008/0051886 A1 | 2/2008 | Lin |
| 2008/0154364 A1 | 6/2008 | Richardson et al. |
| 2008/0200982 A1 | 8/2008 | Your |
| 2008/0269887 A1 | 10/2008 | Cumming |
| 2008/0300680 A1 | 12/2008 | Nun |
| 2008/0306587 A1 | 12/2008 | Your |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0043384 A1 | 2/2009 | Niwa et al. |
| 2009/0116118 A1 | 5/2009 | Frazier et al. |
| 2009/0125106 A1 | 5/2009 | Weinschenk, III et al. |
| 2009/0149952 A1 | 6/2009 | Shadduck |
| 2009/0198326 A1 | 8/2009 | Zhou et al. |
| 2009/0204209 A1 | 8/2009 | Tran |
| 2009/0204210 A1 | 8/2009 | Pynson |
| 2009/0264998 A1 | 10/2009 | Mentak et al. |
| 2009/0292355 A1 | 11/2009 | Boyd et al. |
| 2009/0319040 A1 | 12/2009 | Khoury |
| 2010/0004742 A1 | 1/2010 | Cumming |
| 2010/0055449 A1* | 3/2010 | Ota .................. B32B 25/20 428/331 |
| 2010/0057095 A1 | 3/2010 | Khuray et al. |
| 2010/0094412 A1 | 4/2010 | Wensrich |
| 2010/0094413 A1 | 4/2010 | Rombach et al. |
| 2010/0131058 A1 | 5/2010 | Shadduck |
| 2010/0179653 A1 | 7/2010 | Argento et al. |
| 2010/0204787 A1 | 8/2010 | Noy |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0118834 A1 | 5/2011 | Lo et al. |
| 2011/0118836 A1 | 5/2011 | Jain |
| 2011/0224788 A1 | 9/2011 | Webb |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078364 A1 | 3/2012 | Stenger |
| 2012/0095125 A1 | 4/2012 | Hu et al. |
| 2012/0232649 A1 | 9/2012 | Cuevas |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0035760 A1 | 2/2013 | Portney |
| 2013/0038944 A1 | 2/2013 | Chang et al. |
| 2013/0060331 A1 | 3/2013 | Shadduck |
| 2013/0110234 A1 | 5/2013 | DeVita et al. |
| 2013/0110235 A1 | 5/2013 | Shweigerling |

(56) References Cited

U.S. PATENT DOCUMENTS

| | | |
|---|---|---|
| 2013/0116781 A1 | 5/2013 | Nun |
| 2013/0131794 A1 | 5/2013 | Smiley et al. |
| 2013/0190867 A1 | 7/2013 | Peyman |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0172092 A1 | 6/2014 | Carson et al. |
| 2014/0180404 A1 | 6/2014 | Tram |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0180410 A1 | 6/2014 | Gerardi |
| 2014/0227437 A1* | 8/2014 | DeBoer ............ B29D 11/00009 427/162 |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0309734 A1 | 10/2014 | Sohn et al. |
| 2015/0087743 A1 | 3/2015 | Anvar et al. |
| 2015/0105760 A1 | 4/2015 | Rao et al. |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0238310 A1 | 8/2015 | Matthews et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1 | 3/2016 | Salahieh et al. |
| 2016/0074154 A1 | 3/2016 | Woods |
| 2016/0184089 A1 | 6/2016 | Dudee et al. |
| 2016/0184092 A1 | 6/2016 | Smiley et al. |
| 2016/0208138 A1* | 7/2016 | Nishijima ................ C09D 7/61 |
| 2016/0256265 A1 | 9/2016 | Borja et al. |
| 2016/0262875 A1 | 9/2016 | Smith et al. |
| 2016/0281019 A1* | 9/2016 | Deklippel .............. C08G 77/24 |
| 2016/0287380 A1 | 10/2016 | Shi et al. |
| 2016/0317287 A1 | 11/2016 | Silvestrini et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0216021 A1 | 8/2017 | Brady |
| 2017/0290658 A1 | 10/2017 | Hildebrand et al. |
| 2017/0319332 A1 | 11/2017 | Kahook et al. |
| 2017/0342096 A1 | 11/2017 | Silvestrini |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0256315 A1 | 9/2018 | Hildebrand et al. |
| 2018/0271642 A1 | 9/2018 | Wortz et al. |
| 2018/0271645 A1 | 9/2018 | Brady et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0000612 A1 | 1/2019 | Rao et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076243 A1 | 3/2019 | Hadba et al. |
| 2019/0083235 A1 | 3/2019 | Wortz |
| 2019/0099263 A1 | 4/2019 | Brady et al. |

FOREIGN PATENT DOCUMENTS

| | | | |
|---|---|---|---|
| JP | H09-150002 A | 6/1997 | |
| JP | 2013-047290 | 3/2013 | |
| WO | WO 92/17132 | 10/1992 | |
| WO | WO 99/29266 | 6/1999 | |
| WO | WO 2001/034067 | 5/2001 | |
| WO | WO 2004/037127 | 5/2004 | |
| WO | WO 2004/052242 | 6/2004 | |
| WO | WO 2004/054471 | 7/2004 | |
| WO | WO 2004/072689 | 8/2004 | |
| WO | WO 2006/047383 | 5/2006 | |
| WO | WO 2007/005778 | 1/2007 | |
| WO | WO 2007/047529 | 4/2007 | |
| WO | WO 2007/047530 | 4/2007 | |
| WO | WO 2008/024766 | 2/2008 | |
| WO | WO 2008/031231 | 3/2008 | |
| WO | WO 2008/077040 | 6/2008 | |
| WO | WO 2008/082957 | 7/2008 | |
| WO | WO 2008/103798 | 8/2008 | |
| WO | WO 2009/015161 | 1/2009 | |
| WO | WO 2009/015226 | 1/2009 | |
| WO | WO 2009/015234 | 1/2009 | |
| WO | WO 2009/015240 | 1/2009 | |
| WO | WO 2009/064876 | 5/2009 | |
| WO | WO 2010/010565 | 1/2010 | |
| WO | WO 2010/081093 | 7/2010 | |
| WO | WO 2011/026068 | 3/2011 | |
| WO | WO 2011/106435 | 9/2011 | |
| WO | WO 2011/137191 | 11/2011 | |
| WO | WO 2012/006616 | 1/2012 | |
| WO | WO 2012/129407 | 9/2012 | |
| WO | WO 2013/016804 | 2/2013 | |
| WO | WO 2013/070924 | 5/2013 | |
| WO | WO 2013/142323 | 9/2013 | |
| WO | WO 2013/166068 | 11/2013 | |
| WO | WO 2013/190130 | 12/2013 | |
| WO | WO-2013180254 A2 * | 12/2013 | ............ C08L 83/08 |
| WO | WO 2014/099630 | 6/2014 | |
| WO | WO 2014/145562 | 9/2014 | |
| WO | WO 2014/152017 | 9/2014 | |
| WO | WO 2014/197170 | 12/2014 | |
| WO | WO 2015/066502 | 5/2015 | |
| WO | WO 2015/066532 | 5/2015 | |
| WO | WO 2015/126604 | 8/2015 | |
| WO | WO 2016/018932 | 2/2016 | |
| WO | WO 2016/033217 | 3/2016 | |
| WO | WO 2016/122805 | 8/2016 | |
| WO | WO 2016/201351 | 12/2016 | |
| WO | WO 2017/079449 | 5/2017 | |
| WO | WO 2017/079733 | 5/2017 | |
| WO | WO 2017/087358 | 5/2017 | |
| WO | WO 2017/096087 | 6/2017 | |
| WO | WO 2017/192855 | 11/2017 | |
| WO | WO 2018/081595 | 5/2018 | |
| WO | WO 2018/119408 | 6/2018 | |
| WO | WO 2018/167099 | 9/2018 | |
| WO | WO 2018/222579 | 12/2018 | |
| WO | WO 2018/227014 | 12/2018 | |

(56) References Cited

FOREIGN PATENT DOCUMENTS

| WO | WO 2019/005859 | 1/2019 |
|---|---|---|
| WO | WO 2019/027845 | 2/2019 |

OTHER PUBLICATIONS

Ehrmann, et al., "Ex Vivo Accommodation Simulator II—Concept and Preliminary Results", Proceedings of SPIE vol. 5314, Ophthalmic Technologies XIV, Jul. 2004, pp. 48-58.

Gabel, et al., "Silicone oil with high specific gravity for intraocular use", British Journal of Ophthalmology, Apr. 1987, vol. 71, 262-267.

Ghallagher-Wetmore, et al., "Supercritical fluid processing: a new dry technique for photoresist developing", SPIE's 1995 Symposium on Microlithography, 1995, vol. 2438, 16 pages.

Lane, et al., "Comparison of the biomechanical behavior of foldable intraocular lenses" Journal of Cataract Refract Surg, Nov. 2004, vol. 30, 2397-2402.

Nakamura, et al., "Analysis and Fractionation of Silicone and Fluorosilicone Oils for Intraocular Use", Investigative Ophthalmology & Visual Science, vol. 31, No. 10, Oct. 1990, 2059-2069.

Zhang, et al., "Fluidic adaptive lens with high focal length tunability", Applied Physics Letters, May 2003, vol. 82, No. 19, pp. 3171-3172.

Zhang, et al., "Integrated fluidic adaptive zoom lens", Optics Letters, Dec. 2004, vol. 29, No. 24, pp. 2855-2857.

Zhao, et al., "Strategies for Supercritical $CO_2$ Fractionation of Polydimethylsiloxane," Journal of Applied Polymer Science, 1995, vol. 55, 773-778.

\* cited by examiner

POLYMERIC MATERIAL FOR ACCOMMODATING INTRAOCULAR LENSES

FIELD

The disclosure relates generally to a polymeric material for use in accommodating intraocular lenses for implantation in a lens chamber of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to increase as average life expectancies continue to rise. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lenses. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

SUMMARY

The present disclosure is directed to a polymeric material which comprises a fluorosilicone polymer and a silica component. The presently disclosed polymeric material is both optically clear and has a sufficiently low Young's modulus such that it can effectively respond to the eye's natural accommodative forces and thus can be used in accommodating intraocular lenses. When used in the fabrication of an intraocular lenses, the polymeric material disclosed herein protect the physical characteristics of the lens as the added hydrophobicity of the fluorosilicone polymer allows it to effectively resist diffusion of fluid from the eye and the adhesion of biological materials.

Accordingly, in one aspect, provided herein is a polymeric material comprising a fluorosilicone polymer and up to about 30 weight % of a silica component, wherein the silica component has a surface area of at least about 280 $m^2/g$.

In another aspect, provided herein is an implantable intraocular lens (IOL) comprising a polymeric material comprising a fluorosilicone polymer and up to about 30 weight % of a silica component, wherein the silica component has a surface area of at least about 280 $m^2/g$.

In still another aspect, provided herein is an intraocular lens (IOL) device comprising a fluorosilicone polymer and up to about 30 weight % of a silica component, wherein the silica component has a surface area of at least about 280 $m^2/g$. In one aspect, the intraocular lens (IOL) device comprises (a) a first lens comprised of a fluorosilicone polymer and up to about 30 weight % of a silica component, wherein the silica component has a surface area of at least about 280 $m^2/g$ having a first Young's modulus;

(b) a second lens in spaced relation to the first lens along a central optical axis; and (c) a circumferential portion encircling the first and second lens, the circumferential portion comprising an outer peripheral edge;

wherein at least one of a portion of the second lens and a portion of the circumferential portion is made of a material having a second Young's modulus; and wherein the first Young's modulus is less than the second Young's modulus.

Other objects, features and advantages of the described embodiments will become apparent to those skilled in the art from the following detailed description. It is to be understood, however, that the detailed description and specific examples, while indicating various embodiments of the present invention, are given by way of illustration and not imitation. Many changes and modifications within the scope of the present invention may be made without departing from the spirit thereof, and the invention includes all such modifications.

DETAILED DESCRIPTION

Specific, non-limiting embodiments of the present invention will now be described with reference to the drawings. It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Polymeric Material

The present disclosure is directed to a polymeric material comprising a fluorosilicone polymer and a silica component which is both optically clear and has a sufficiently low modulus such that it can effectively respond to the eye's natural accommodative forces and thus be used in accommodating intraocular lenses.

In one embodiment, the presently disclosed polymeric material comprises a fluorosilicone polymer and up to about 30 weight % of a silica component. The fluorosilicone polymer described herein is a crosslinked copolymer of dialkyl, diphenyl or phenylalkyl siloxane and a fluorinated dialkyl siloxane. Typically, the fluorosilicone polymer is a crosslinked copolymer of dialkyl, diphenyl or phenylalkyl siloxane and trifluoroalkyl(alkyl)siloxane, but can be a terpolymer or higher order polymer of diphenyl and/or phenylalkyl siloxane, dialkyl siloxane and trifluoroalkyl(alkyl)

siloxane. In certain embodiments, the fluorosilicone polymer is a crosslinked copolymer of dialkyl siloxane, such as dimethyl siloxane, and trifluoroalkyl(alkyl)siloxane, such as 3,3,3-trifluoropropylmethyl siloxane. The ratio of dialkyl siloxane and trifluoroalkyl(alkyl)siloxane can be adjusted to tune the physical properties of the fluorosilicone polymer. For example, increasing the trifluoroalkyl(alkyl)siloxane can increase the hydrophobicity of the resulting fluorosilicone polymer. In some embodiments, the fluorosilicone polymer typically comprises at least about 25 mole % trifluoroalkyl(alkyl)siloxane, or about 25 mole % trifluoroalkyl(alkyl)siloxane, or about 30 mole % trifluoroalkyl(alkyl)siloxane, or about 35 mole % trifluoroalkyl(alkyl)siloxane, or about 40 mole % trifluoroalkyl(alkyl)siloxane, or about 50 mole % trifluoroalkyl(alkyl)siloxane or from about 25 mole % to about 50 mole %, or from about 25 mole % to about 40 mole % trifluoroalkyl(alkyl)siloxane.

In one embodiment, the fluorosilicone polymer is represented by formula (I):

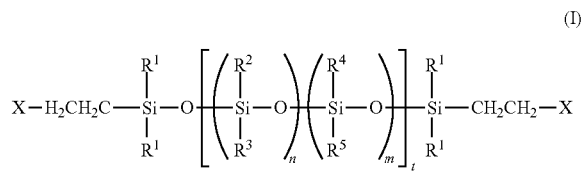

wherein:

n and m are each independently 0 to about 500;

t is about 100 to about 1000;

each $R^1$ is independently alkyl or aryl;

$R^2$ is haloalkyl;

$R^3$ is alkyl or haloalkyl;

$R^4$ and $R^5$ are independently alkyl, haloalkyl or aryl; and each X is a crosslinker which links the polymer of formula (I) with a second polymer of formula (I).

In one embodiment, n is about 50, or about 100, or about 125, or about 150, or about 200, or about 250, or about 300, or about 350, or about 400, or about 450, or about 500. In one embodiment, m is about 50, or about 100, or about 125, or about 150, or about 200, or about 250, or about 300, or about 350, or about 400, or about 450, or about 500. In another embodiment, n is about 100, and m is about 150.

In any embodiment, t is about 100, or about 125, or about 150, or about 200, or about 250, or about 300, or about 350, or about 400, or about 450, or about 500, or about 550, or about 600, or about 650, or about 700, or about 750, or about 800, or about 850, or about 900, or about 950, or about 1000.

In one embodiment, each $R^1$ is alkyl. Suitable alkyl groups include, but are not limited to, $C_1$-$C_6$ alkyl groups such as methyl, ethyl, n-propyl, i-propyl, n-butyl, t-butyl, n-pentyl, n-hexyl, and the like. In another embodiment, each $R^1$ is methyl. In one embodiment, $R^3$ is alkyl, such as defined for $R^1$. In another embodiment, $R^3$ is methyl. In one embodiment, $R^4$ is alkyl, such as defined for $R^1$. In another embodiment, $R^4$ is methyl. In one embodiment, $R^5$ is alkyl, such as defined for $R^1$. In another embodiment, $R^5$ is methyl. In yet another embodiment, $R^4$ and $R^5$ are methyl. In still another embodiment, the fluorosilicone polymer is represented by formula (IA):

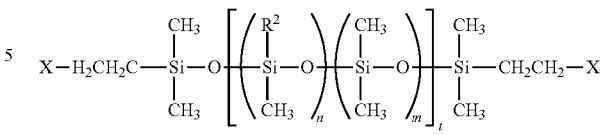

wherein:

n is from 1 to about 500;

m is from 0 to about 500;

t is about 100 to about 1000;

$R^2$ is haloalkyl;

$R^3$ is alkyl or haloalkyl; and each X is a crosslinker which links the polymer of formula (IA) with a second polymer of formula (IA).

In one embodiment, $R^2$ is a haloalkyl group comprising from 1 to 3 halo (provided at least one is fluoro) substituents. Exemplary haloalkyl groups include, but are not limited to, fluoromethyl, 2-fluorethyl, 2,2-difluoroethyl, and 3,3,3-trifluoropropyl. In one embodiment, $R^2$ is 3,3,3-trifluoropropyl.

The crosslinker is typically a methylhydrosiloxane-dimethylsiloxane copolymer with a methyl-hydrogen content of from about 30 to about 70 mole %. In some embodiments, the crosslinker has a chain length of from about 5 to about 30 repeating Si units (i.e., degree of polymerization).

In certain embodiments, the polymeric material provided herein has a degree of polymerization of from about 200 to about 500, or from about 300 to about 500, or about 400, or about 450.

In order to be used as an intraocular lens material, the polymeric material described herein should be optically clear. However, the fluorosilicone polymer and the silica component are not index matched. Thus the optical properties of the polymeric material must be maintained as the modulus is increased. Advantageously, the optical properties of the presently disclosed polymeric material can be tuned independently from the modulus. Several different factors contribute to the optical properties of the polymeric material, including the amount and particle size of the silica component.

Since the refractive index of the fluorosilicone polymer is low, it is contemplated that the particle size of the silica component should be as small as possible in order to obtain superior optical characteristics. In certain embodiments, the polymeric material provided herein has a refractive index of from about 1.35 to about 1.40, or from about 1.37 to from about 1.39, or about 1.38. Accordingly, the silica component as used herein has a surface area of at least about 280 $m^2$/g, or at least about 300 $m^2$/g, or at least about 310 $m^2$/g, or at least about 320 $m^2$/g, or at least about 330 $m^2$/g, or at least about 340 $m^2$/g, or at least about 350 $m^2$/g. In certain embodiments, the silica component has an average particle size of less than about 11 nanometers. Fumed silica having an average particle size of about 7 nanometers in diameter is particularly suitable because the small particle size does not interfere with the wavelength of visible light and contributes to an improved optical resolution in the cured composition. Commercial fumed silica with particle sizes as low as 7 nm are commercially available (e.g., CABOT and Sigma). Typically, the silica component is present in an amount up to about 30 weight %, or 27 weight %, or about 25 weight %, or about 23 weight %, or about 20 weight %, or from about 20 to about 30 weight %.

The silica component as used herein is fumed or "activated" silica, which has been treated with a silazane. The amount of silica component should be such that the polymeric material is sufficiently reinforced, yet remains optically clear. Suitable silazanes and methods for carrying out the fumed silica treatment include the in situ reaction of small particle size fumed silica and are well known in the art. In such reactions, the silazane (e.g., hexamethyldisilazane) readily reacts with the hydroxyl functionalities on fumed silica, forming a trimethylsiloxane coating on the silica surface. In certain embodiments, the polymeric material provided herein has a Young's modulus of from about 10 psi to about 150 psi, or from about 50 psi to about 100 psi, or about 70 psi.

Other physical characteristics of the polymeric material can be modulated as well. In certain embodiments, the polymeric material provided herein has a tensile strength of from about 500 psi to about 1200 psi, or from about 700 psi to about 1000 psi, or about 900 psi. In certain embodiments, the polymeric material provided herein has a percent elongation of from about 400% to about 1000%, or about 600%.

Also provided herein are methods for making the above-described polymeric material. In certain embodiments, the method comprises the steps of:

(a) combining a vinyl end-capped fluorosilicone polymer with up to about 30 weight % of a silica component, wherein the silica component has a surface area of at least about 280 m²/g, to obtain a fluorosilicone base composition;

(b) adding a crosslinking agent and a curing agent to the fluorosilicone base composition; and (c) curing the fluorosilicone base composition to obtain the polymeric material.

The vinyl end-capped fluorosilicone polymer can be synthesized using known methods from commercially available starting materials or purchased from commercial sources. For example, a vinyl end-capped trifluoropropylmethylsiloxane—dimethylsiloxane copolymer having a molecular weight of about 25,000 to about 35,000—is commercially available from Gelest. Alternatively, the vinyl end-capped fluorosilicone polymercan be synthesized as described in Example 1, for example. Suitable starting materials include, but are not limited to, alkylsiloxanes (e.g., octamethylcyclotetrasiloxane), haloalkylsiloxanes (e.g., trifluoropropyltrimethylcyclosiloxane), and the like. Suitable vinyl endblockers include, but are not limited to, vinyl-endblocked dimethyl siloxane oligomer.

In one embodiment, the fluorosilicone polymer has a long chain length, having a molecular weight of greater than 35,000 daltons, or greater than 50,000 daltons and, or greater than 70,000 daltons are desired.

In one embodiment, the fluorosilicone polymer is a compound of formula (II):

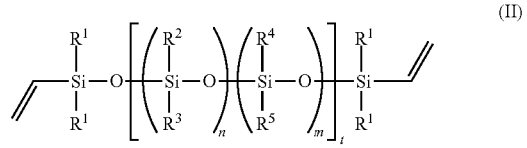

(II)

wherein:
n and m are each independently 0 to about 500;
t is from about 100 to about 1000;
each $R^1$ is independently alkyl or aryl;
$R^2$ is haloalkyl;
$R^3$ is alkyl or haloalkyl; and
$R^4$ and $R^5$ are independently alkyl, haloalkyl or aryl.

The polymeric material described herein has a degree of crosslinking such that the material has a sufficiently low modulus to minimize any potential deformation caused by forces applied during its use as, for example, an accommodating intraocular lens, yet also be sufficiently solid as to minimize the permeation of the gel. In certain embodiments, the polymeric material is lightly crosslinked, having less than about 5 parts per hundred (pph) crosslinker, or less than about 4 pph, or less than about 2 pph, or less than about 1 pp, or about 1 pph. The crosslinker is typically a methylhydrosiloxane-dimethylsiloxane copolymer with a methylhydrogen content of from about 30 to about 70 mole %. In some embodiments, the crosslinker has a chain length of from about 5 to about 30 repeating Si units (i.e., degree of polymerization).

In one embodiment, the curing step comprises adding a platinum catalyst. The platinum group metal catalyst can be any of the compatible platinum group metal-containing catalysts known to catalyze the addition of silicone-hydrogen atoms to silicon-bonded vinyl radicals. Platinum group metal-containing catalysts can be any of the known forms which are compatible, such as platinic chloride, salts of platinum, chloroplatinic acid and various complexes, for example, silicone complexes with platinum metal-containing groups. The platinum group metal-containing catalyst can be used in any catalytic quantity, such as in an amount sufficient to provide at least about 0.1 ppm weight of platinum group metal (as elemental metal) based on the total weight of the composition. In certain embodiments, at least about 10 ppm, or at least about 20 ppm, or at least 30 ppm, or at least about 40 ppm by weight of platinum catalyst was used.

Implantable Intraocular Lens (IOL)

A device implanted in the eye naturally becomes exposed to the fluid in the eye and the fluid can, over time, diffuse through the device and have unintended and/or undesired effects on the physical characteristics of the device. Attempts have been made to coat ophthalmic devices with barrier layers to prevent such diffusion, but these procedures can be costly and time consuming. In addition, if an ophthalmic device contains a chamber or channel within the device which contains a fluid, there is a risk that that fluid can diffuse out of its fluid chamber and into the polymeric material. This results in a decrease in the amount of fluid that can be utilized by the IOL, as well as to possibly alter the physical characteristics of the polymeric material. Fluorocarbon-containing silicone monomers can enhance a polymer's resistance to the diffusion of fluid, and as such, the polymeric material described herein can be used in ophthalmic devices to resist the diffusion of fluid into or out of the device.

The IOLs can be fabricated from the disclosed polymeric material using known molding techniques, such as disposable or polished stainless steel mold, having a mold cavity in the shape required for the correct refraction of light for the material. In practice, the uncured fluorosilicone base composition is introduced into the mold cavity, in an amount dictated by considerations relating to the lens size, refractive power, and structure, and then cured. Several methods of molding the lens can be employed, including injection molding, liquid injection molding, compression molding, and transfer molding.

Intraocular Lens (IOL) Device

The presently disclosed intraocular lenses can be used in an intraocular device for implantation in a patent. Such devices are known in the art, and include, for example, those described in U.S. Pat. Nos. 7,662,180 and 7,875,661.

In certain embodiments, the presently disclosed intraocular lenses can be used as a power changing lens in a two-part accommodating IOL device in which the power changing lens and a primary lens are in sliding contact with one another within a lens chamber. In such systems, the power changing lens is sized and shaped to take on and respond to the radially-inward forces which are applied along the peripheral edge of the lens. In contrast, the primary lens does not participate in providing an accommodative response and thus is sized and shaped so as to avoid interfering or resisting the radial compressive forces that are applied to the power changing lens. This may be accomplished by controlling the relative diameters and thicknesses of the power changing lens and the primary lens to maximize the extent to which the radial compressive forces are applied onto the power changing lens and to minimize the extent to which these forces are applied onto the primary lens.

Accordingly, in one embodiment, provided herein is an intraocular lens (IOL) device comprising:

(a) a first lens comprised of the polymeric material as described herein having a first Young's modulus;

(b) a second lens in spaced relation to the first lens along a central optical axis; and (c) a circumferential portion encircling the first and second lens, the circumferential portion comprising an outer peripheral edge;

wherein at least one of a portion of the second lens and a portion of the circumferential portion is made of a material having a second Young's modulus; and wherein the first Young's modulus is less than the second Young's modulus.

In practice, the first lens (i.e., the power changing lens) and the second lens (i.e., the primary lens) are in sliding contact with one another within a lens chamber. The lens chamber is filled with a fluid or gel having specific physical and chemical characteristics to enhance the range of refractive power provided by the IOL during accommodation. The fluid or gel is selected such that it cooperates with the power changing lens in providing a sufficient range of accommodation of up to at least 3 diopters, preferably up to at least 5 diopters, preferably up to at least 10 diopters and most preferably up to at least 15 diopters.

In addition, a lens comprised of the polymeric material described herein has a reduced likelihood of buckling in a patient from contact with the primary lens as the surface is significantly more oleophobic than other polymers typically used for IOLs.

In addition to use in an IOL, the polymeric material of the present disclosure can also be used in other ophthalmic devices such as, but not limited to, contact lenses, keratoprostheses, capsular bag extension rings, corneal inlays, corneal rings, or other ophthalmic devices. An exemplary alternative use would be in the field of breast implants, such that the polymers can be used as an exterior shell-like material to prevent leakage of an internal material.

EXAMPLES

Example 1

An exemplary polymeric material according to the present disclosure was prepared as follows.

Vinyl Endblocked 40 mole % Fluorosilicone Polymer

A vinyl endblocked 40 mole % fluorosilicone polymer for use in the fluorosilicone base was prepared as follows. 140 parts octamethylcyclotetrasiloxane (D4 cyclics), 100 parts trifluoropropyltrimethylcyclosiloxane (D3 fluorocyclics), 3.2 parts vinyl-endblocked dimethyl siloxane oligomer (vinyl endblocker), and 0.1 parts potassium siloxanolate catalyst were agitated in a polymerization vessel and heated to about 150° C. At 150° C., potassium siloxanolate catalyst was added to the polymerization vessel. Once polymerization was visually observed by an increased viscosity, polymerization was continued for about 3 hours.

After about 3 hours, the catalyst was de-activated by purging polymer with $CO_2$ for 1 hour and the polymer exposed to reduced pressure (minimum of 27" Hg vacuum) at a temperature of from about 150° C. to about 180° C. until the volatile content reached an amount below about 3%.

Fluorosilicone Base 100 parts of the vinyl endblocked 40 mole % fluorosilicone polymer, 9 parts hexamethyldisilizane (HMDZ) and 3 parts water were added to a mixing vessel (e.g., sigma blade mixer). Once mixed, 60 parts activated silica (Tokuyama QS-30C fumed silica) was added in multiple additions until the silica was fully mixed into the fluorosilicone polymer. The composition was mixed at 80° C. for about 30 minutes, at which time the mixing vessel was heated to about 150° C. for about 3 hours under vacuum.

After about 3 hours, the heat and vacuum were removed. While the fluorosilicone base was still hot, additional fluorosilicone polymer was slowly added to the polymerization vessel until the silica content was reduced to approximately 25 parts. The fluorosilicone base was then dispersed in chlorinated solvent (i.e., perchloroethylene) to approximately 30% solids content, filtered through 1 micron media filter and subjected to heat and vacuum to remove solvent.

Polymeric Material Comprising a Fluorosilicone Polymer

Equal parts of A and B (Table 1) were mixed together, vacuum de-aired, and press cured in an ASTM test slab mold for about 10 minutes at 302° F. Cured test slab was allowed to equilibrate at room temperature for a minimum of 3 hours.

TABLE 1

| Part A | Part B |
| --- | --- |
| 100 part fluorosilicone base | 100 parts fluorosilicone base |
| 5-15 ppm platinum catalyst | 2 parts methyl hydrogen siloxane crosslinker |
|  | 0.3 pph methyl vinyl cyclosilicone inhibitor |

Mechanical properties of the fluorosilicone polymer are shown in Table 2. Surprisingly, the fluorosilicone polymer as described herein exhibits an enhanced tensile strength while maintaining a low modulus when compared to a non-fluorinated silicone polymer. In addition, it is contemplated that the fluorosilicone polymer described herein maintains a suitable optical clarity due to the low silica content.

|  | Fluorosilicone polymer | Non-fluorinated silicone polymer |
| --- | --- | --- |
| Durometer (Shore A) | 20 | 20 |
| Tensile strength | 900 psi | 475 psi |
| % elongation | 600% | 300% |
| 100% modulus | 70 psi | 65 psi |

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

The invention claimed is:

1. A polymeric material comprising a fluorosilicone polymer and up to about 30 weight % of a silica component, wherein the silica component has a surface area of at least about 280 m²/g, and wherein the fluorosilicone polymer comprises a polymer of formula

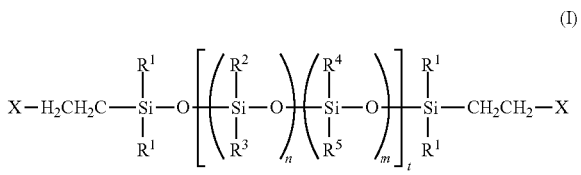

(I)

wherein:
n and m are each independently 0 to about 500;
t is about 100 to about 1000;
each $R^1$ is independently alkyl or aryl; each $R^2$ is independently fluoroalkyl;
each $R^3$ is independently alkyl or fluoroalkyl;
each $R^4$ and $R^5$ is independently alkyl, fluoroalkyl or aryl;
at least one $R^1$, $R^4$ or $R^5$ is aryl; and
each X is a crosslinker which links the polymer of formula (I) with a second polymer of formula (I);
wherein the polymeric material has a Young's modulus of from about 10 psi to about 150 psi.

2. The polymeric material of claim 1, wherein the silica component has a surface area of from about 280 m²/g to about 350 m²/g.

3. The polymeric material of claim 1, comprising about 20% to about 27% of the silica component.

4. The polymeric material of claim 1, wherein the fluorosilicone polymer comprises a crosslinked copolymer of dialkyl, diphenyl or phenylalkyl siloxane and fluorinated dialkyl siloxane.

5. The polymeric material of claim 1, wherein the fluorosilicone polymer comprises a crosslinked copolymer of diphenyl, phenylalkyl, or dialkyl siloxane and trifluoroalkyl (alkyl)siloxane.

6. The polymeric material of claim 1, wherein $R^2$ is 3,3,3-trifluoropropyl.

7. The polymeric material of claim 6, comprising at least about 25 mole % trifluoropropyl content.

8. The polymeric material of claim 1, having a refractive index of from about 1.35 to about 1.40.

9. The polymeric material of claim 1, having a tensile strength of from about 500 psi to about 1200 psi.

10. The polymeric material of claim 1, having a percent elongation of from about 400% to about 1000%.

11. The polymeric material of claim 1, having a degree of polymerization of from about 200 to about 500.

12. The polymeric material of claim 1, having a Young's modulus of from about 50 psi to about 100 psi.

13. The polymeric material of claim 1, wherein the crosslinker is a methylhydrosiloxane-dimethylsiloxane copolymer.

14. The polymeric material of claim 13, wherein the crosslinker has a chain length of from about 5 to about 30 repeating Si units.

15. The polymeric material of claim 13, wherein the crosslinker has a methyl-hydrogen content of from about 30 to about 70 mole %.

16. An implantable intraocular lens (IOL) comprising the polymeric material of claim 1.

17. A method of making the polymeric material of claim 1, comprising the steps of:
(a) combining a vinyl end-capped fluorosilicone polymer with up to about 30 weight % of a silica component, wherein the silica component has a surface area of at least about 280 m²/g, to obtain a fluorosilicone base composition;
(b) adding a crosslinking agent and a curing agent to the fluorosilicone base composition; and
(c) curing the fluorosilicone base composition to obtain the polymeric material.

18. An intraocular lens (IOL) device comprising:
(a) a first lens comprising the polymeric material of claim 1 having a first Young's modulus;
(b) a second lens in spaced relation to the first lens along a central optical axis; and
(c) a circumferential portion encircling the first and second lens, the circumferential portion comprising an outer peripheral edge;
wherein at least one of a portion of the second lens and a portion of the circumferential portion is made of a material having a second Young's modulus; and
wherein the first Young's modulus is less than the second Young's modulus.

19. A polymeric material comprising a crosslinked copolymer of dialkyl, diphenyl or phenylalkyl siloxane and fluorinated dialkyl siloxane, and up to about 30 weight % of a silica component, wherein the silica component has a surface area of at least about 280 m²/g, and wherein the polymeric material has a Young's modulus of from about 10 psi to about 150 psi.

20. A polymeric material comprising a crosslinked copolymer of diphenyl, phenylalkyl, or dialkyl siloxane and trifluoroalkyl(alkyl)siloxane and up to about 30 weight % of a silica component, wherein the silica component has a surface area of at least about 280 m²/g, and wherein the polymeric material has a Young's modulus of from about 10 psi to about 150 psi.

21. A polymeric material comprising a crosslinked terpolymer of diphenyl and/or phenylalkyl siloxane, dialkyl siloxane, and trifluoroalkyl(alkyl) siloxane, and up to about 30 weight % of a silica component, wherein the silica component has a surface area of at least about 280 m²/g, and wherein the polymeric material has a Young's modulus of from about 10 psi to about 150 psi.

* * * * *